United States Patent [19]

Graham et al.

[11] 4,407,802

[45] Oct. 4, 1983

[54] 6-AMIDINO-9-SUBSTITUTED BENZYL PURINES

[75] Inventors: Donald W. Graham, Mountainside; Gary H. Rasmusson, Watchung; Richard L. Tolman, Warren, all of N.J.

[73] Assignee: Merck & Co., Inc., Rahway, N.J.

[21] Appl. No.: 306,112

[22] Filed: Sep. 28, 1981

[51] Int. Cl.³ .................. C07D 473/34; A61K 31/52
[52] U.S. Cl. .................................... 424/253; 544/277
[58] Field of Search ........................ 544/277; 424/253

[56] References Cited

U.S. PATENT DOCUMENTS

| | | | |
|---|---|---|---|
| 3,846,426 | 11/1974 | Lira et al. ............................ | 424/253 |
| 3,862,189 | 1/1975 | Schwender ........................ | 544/277 |
| 4,189,485 | 2/1980 | Matsuno et al. .................... | 544/277 |

FOREIGN PATENT DOCUMENTS 1534163 11/1978 United Kingdom.

OTHER PUBLICATIONS

Meerwein et al, Ann. 641, 1, (1961).
Bredereck et al, Angew. Chem., 73, 493 (1961).
Neilson, Chemistry of Amidines and Imidates, Patai Ed., pp. 385–413 (1975).
Imai et al, European J. Med. Chems., 15, 207–210 (1980).

*Primary Examiner*—Mary C. Lee
*Attorney, Agent, or Firm*—David L. Rose; Mario A. Monaco

[57] ABSTRACT

This invention is concerned with 6-(substituted amidino-9-substituted benzyl purine derivatives and in particular 6-(aminomethylideneamino)-9-substituted benzyl purines. The compounds are active anticoccidial agents and suitable compositions and methods are described for the administration of such compounds to poultry for the prevention and treatment of coccidiosis.

6 Claims, No Drawings

6-AMIDINO-9-SUBSTITUTED BENZYL PURINES

BACKGROUND OF THE INVENTION

The use of 6-amino-9-substituted benzyl purines for the treatment of coccidiosis is well known. See U.S. Pat. No. 3,846,426 to Lira et al. issued Nov. 5, 1974. In particular, the compound 6-amino-9-(2-chloro-6-fluorobenzyl)purine is described which is particularly active and is currently sold under the generic name of arprinocid. In addition, certain $N^6$ methyl arprinocid derivatives are disclosed. See Great Britain Pat. No. 1,534,163. The instant $N^6$ amidino compounds are highly active anticoccidial compounds in their own right and are also intermediates in the preparation of the $N^6$ methyl arprinocid compound from arprinocid.

SUMMARY OF THE INVENTION

The instant disclosure is concerned with 6-amidino-9-substituted benzyl purines which compounds are active anticoccidial agents. Thus, it is an object of this invention to describe such compounds. It is a further object of the invention to describe processes for the preparation of such compounds. It is a still further object of this invention to describe compositions and methods of treatment using the compounds of this invention for the administration to poultry, in particular chickens, for the treatment of coccidiosis. Further objects of the invention will become apparent from a reading of the following description.

DESCRIPTION OF THE INVENTION

The instant invention is best described in the following structural formula:

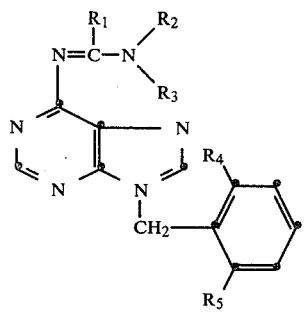

wherein $R_1$, $R_2$ and $R_3$ are independently hydrogen and loweralkyl and $R_4$ and $R_5$ are independently halogen.

It will be appreciated by those skilled in the art that when $R_2$ or $R_3$ is hydrogen, the above 6-amidino derivatives also exist in the corresponding tautomeric form. The definition of the substituents remains the same, however, the structure may be represented as:

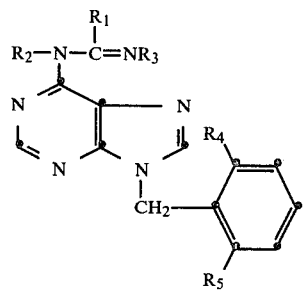

When $R_2$ is hydrogen the two above structures are interchangeable and in fact the compound may exist in both forms simultaneously. When $R_2$ is other than hydrogen, structure II can be permanently prepared and isolated using the procedure described below.

When used in the instant application, the term "loweralkyl" is intended to include those alkyl groups containing from 1 to 6 carbon atoms exemplified by methyl, ethyl, propyl, isopropyl, butyl, pentyl, hexyl and the like.

The term "halogen" when employed in the instant application is intended to include the halogen atoms, fluorine, chlorine, bromine and iodine.

The preferred compounds of this invention are realized in the above-structural formula wherein $R_1$ is hydrogen or loweralkyl; $R_2$ and $R_3$ are loweralkyl; and $R_4$ and $R_5$ are fluorine or chlorine.

Still further preferred compounds of the instant invention are realized when $R_1$ is hydrogen or methyl, $R_2$ and $R_3$ are independently methyl or ethyl, $R_4$ is fluorine and $R_5$ is chlorine.

The compounds of the instant invention are prepared from a 6-amino-9-substituted benzyl purine and an acetal of an aliphatic amide as outlined in the following reaction scheme.

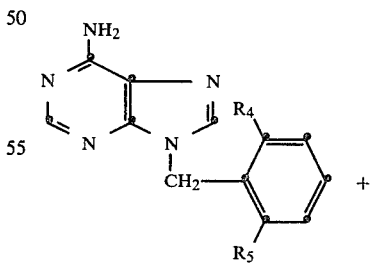

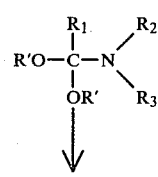

-continued

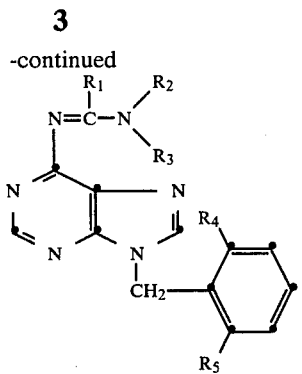

wherein $R_1$, $R_2$, $R_3$, $R_4$ and $R_5$ are as previously defined and $R'$ is loweralkyl.

The foregoing reaction is carried out by mixing the two reactants neat or by dissolving them in a co-solvent. The reaction may be carried out equally well using either procedure, and the choice of whether to use a co-solvent or not depends more on the availability of the acetal of the aliphatic amide than upon the differences in reaction rates to be expected. If the aliphatic amide acetal is relatively expensive, the choice would be to use a co-solvent. Where a co-solvent is to be employed the preferred co-solvents are N,N-dimethylformamide, dimethylacetamide (except in those cases where acetal exchange occurs), sulfolane, methylpyrrolidone, dimethylsulfoxide, hexamethylphosphoramide and the like. The preferred solvents are N,N-dimethylformamide and dimethylsulfoxide. The reaction is preferably carried out at room temperature in order to maximize the yields and minimize the production of reaction by-products. However, if desired, the reaction may be carried out up to the boiling point of the reaction mixture. The reaction is generally complete in from 1 to 48 hours, however, most reactions are complete in about 24 hours. The desired product is isolated from the reaction mixture using techniques known to those skilled in the art.

The acetal reactant in the foregoing reaction scheme may be prepared using techniques described in the literature. References for the production of the above acetals of alipatic amides by O-alkylation of an aliphatic tertiary amide to give a carbonium ion which is neutralized with alkoxide are Meerwein et al., *Ann.*, 641, 1, (1961) and Bredereck et al., *Angew Chem*, 73, 493 (1961).

The 6-amino-9-substituted benzyl purines used as starting materials are also known compounds which are described in U.S. Pat. No. 3,846,426, issued Nov. 5, 1974 to Lira et al.

Other procedures are also available for the preparation of the compounds of this invention. Another such process involves the use of Compound II or III above, in reaction with an alkyl imidate or alkyl imidate salt of the formula:

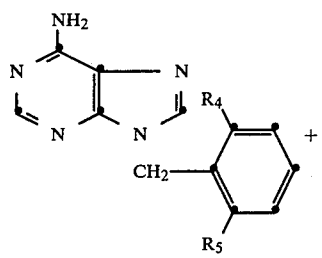

wherein $R_1$ and $R_3$ are as previously defined and $R''$ is loweralkyl or phenyl. The reaction is carried out in a solvent, preferably an alcohol such as methanol or ethanol, and is complete in from 1 to 48 hours. The reaction is preferably carried out at the reflux temperature of the reaction mixture however temperatures of from RT to reflux are successful.

The imidate reactants are prepared by known procedures such as the well-known Pinner Reaction from alkyl nitriles. The reactants are also prepared by the o-alkylation of primary and secondary amides using triethyloxonium fluoroborate or dialkylsulfate. See D. A. Nelson in *Chemistry of Amidines and Imidates*, S. Patai ed. page 385 (1975).

Another procedure for the preparation of the instant compound involves the reaction of compound III with an orthoester followed by reaction with an amine.

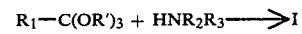

$$R_1-C(OR')_3 + HNR_2R_3 \longrightarrow I$$

wherein $R_1$, $R_2$, $R_3$, $R_4$, $R_5$ and $R'$ are as previously defined. The reaction is carried out in two steps; the first being the reaction with the orthoester. This step is generally carried out neat, or optionally with an inert solvent, with an excess of the orthoester. The reaction is heated to reflux for from 1 to 24 hours. Then the reaction mixture is cooled to room temperature, the excess orthoester and solvent removed, and the amine added. The use of a solvent for this step is optional, however if a solvent is employed, dioxane, sulfolane, dimethyl sulfoxide and the like are preferred. If a solvent is used the reaction is generally slower and from 1–48 hours is generally required for the reaction. The reaction with the amine is generally carried out at room temperature for from 6 to 48 hours. In the tautomeric form of compound II, the above procedure is employed using as the starting material the compound of Formula III with $R_2$ substituted at the 6-position of compound III, $R_2$ being other than hydrogen as set forth in Formula IV.

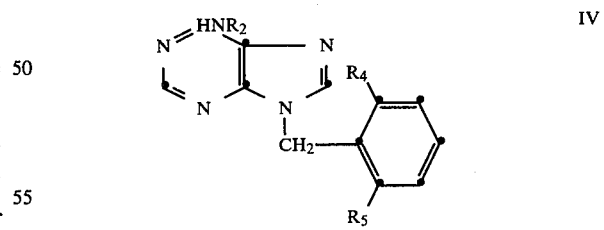

Compound IV can be allowed to react with an alkylimidate of the formula $[R_1\text{-}C(OR'')NR_3]$ to form the compound of Formula II wherein $R_2$ is other than hydrogen.

Coccidiosis is a widespread poultry disease which is produced by infections of protozoa of the genus Eimeria which causes severe pathology in the intestines and ceca of poultry. Some of the most significant of these species are *E. tenella, E. acervulina, E. necatrix, E. brunetti* and *E. maxima*. This disease is generally spread by the birds picking up the infectious organism in droppings on contaminated litter or ground, or by way of food or drinking water. The disease is manifested by hemorrhage, accumulation of blood in the ceca, passage of blood in the droppings, weakness and digestive disturbances. The disease often terminates in the death of the animal, but the fowl which survive severe infections have had their market value substantially reduced as a result of the infection. Coccidiosis is, therefore, a disease of great economic importance and extensive work has been done to find new and improved methods for controlling and treating coccidial infections in poultry.

The novel compounds of this invention are orally administered to poultry for the control and prevention of coccidiosis. Any number of conventional methods are suitable for administering the coccidiostats of this invention to poultry, as for example, they may be given in the poultry feed. The actual quantity of the coccidiostats administered to the poultry in accordance with this invention will vary over a wide range and be adjusted to individual needs, depending upon species of the coccidia involved and severity of the infection. The limiting criteria are that the minimum amount is sufficient to control coccidiosis and the maximum amount is such that the coccidiostat does not result in any undesirable effects.

A feed will typically contain from about 0.0005 to about 0.05 percent, preferably from about 0.0025 to about 0.01 percent, by weight of one of the coccidiostats of this invention. The optimum levels will naturally vary with the specific compound utilized and species of Eimeria involved, and can be readily determined by one skilled in the art. Levels of 6-amino-9-(2,6-dichlorobenzyl)purine and its corresponding $N^1$-oxide, which are among the most preferred coccidiostats of this invention, in poultry feed of from about 0.0035 percent to about 0.0075 percent by weight of the diet are especially useful in controlling the pathology associated with *E. tenella*, while the preferred concentration for similar control of intestinal-dwelling species is from about 0.0025 percent to about 0.0065 percent by weight of the diet.

Depending on the compound employed, levels of 0.001 percent to 0.0035 percent possess the novel effects of reducing the number of oocysts passed in the droppings of infected chickens and/or inhibiting the subsequent division and maturation to infectivity, scientifically designated as the process of sporulation. Thus, the combination of prevention of pathology, coupled with the inhibiting effect on the reproductive product of these organisms, the oocysts, present a unique two-fold method for the control of coccidiosis in poultry.

The quantity of concentration of a novel coccidiostat of this invention in any admixture in which it is administered to the poultry will, of course, vary in accordance with the type of admixture utilized.

Of the various methods of administering the coccidiostats of this invention to poultry, they are most conveniently administered as a component of a feed composition. The novel coccidiostats may be readily dispersed by mechanically mixing the same in finely ground form with the poultry feedstuff, or with an intermediate formulation (premix) that is subsequently blended with other components to prepare the final poultry feedstuff that is fed to the poultry. Typical components of poultry feedstuffs include molasses, fermentation residues, corn meal, ground and rolled oats, wheat shorts and middlings, alfalfa, clover and meat scraps, together with mineral supplements such as bone meal and calcium carbonate and vitamins.

The following non-limiting examples will serve to further illustrate the instant invention.

EXAMPLE 1

6-(N,N-dimethylaminomethylidineamino)-9-(2-chloro-6-fluorobenzyl)purine

A mixture of 1.00 g of 6-amino-9-(2-chloro-6-fluorobenzyl)purine in 15 ml of dimethylformamide dimethylacetal is heated at 100° C. After 10 minutes, a solution forms which shortly thereafter starts producing a crystalline precipitate. The heating is continued for 2 hours. The thickened reaction mixture is then cooled in an ice bath and filtered. The solid is washed twice with 8 ml portions of ether. The solid material is dried in vacuo to give 1.139 g of 6-(N,N-dimethylaminomethylidineamino)-9-(2-chloro-6-fluorobenzyl)purine, melting point 172°–173° C.

EXAMPLE 2

6-Aminoethylidenimino-9-(2,6-dichlorobenzyl)purine hydrochloride

A mixture of 9-(2,6-dichlorobenzyl)adenine (1.0 g), ethyl acetimidate hydrochloride (0.5 g), and absolute ethanol (200 ml) is heated at reflux under nitrogen for 18 hours. The product crystallizes during the course of the reaction. The reaction mixture is cooled, filtered and the product washed with a small amount of water and then with ether. Recrystallization from aqueous isopropanol affords homogenous 6-Aminoethylidenimino-9-(2,6-dichlorobenzyl)purine hydrochloride, mp. 198° C.

EXAMPLE 3

6-Ethylaminomethylidenimino-9-(2-chloro-6-fluorobenzyl)purine

One gram of 9-(2-chloro-6-fluorobenzyl) adenine is covered with 25 ml of triethyl orthoformate and heated at reflux for 12 hours. The solution is cooled and evaporated in vacuo to an amorphous solid. This ethoxymethylidene derivative was used without further purification in the next step. Aqueous ethylamine (20 ml of 40%) is added and the mixture allowed to stand at room temperature for 18 hours. The solid which deposited is filtered, dried in vacuo and recrystallized from isopropanol affording 6-Ethylaminomethylidenimino-9-(2-chloro-6-fluorobenzyl)purine, mp. 147°–8° C.

What is claimed is:

1. A compound having the formula

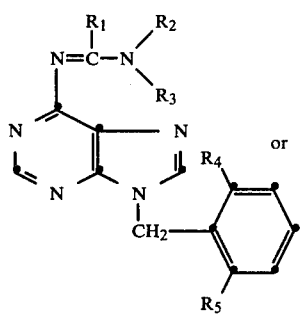

-continued

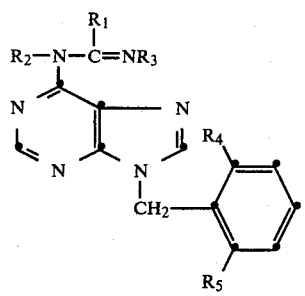

wherein $R_1$, $R_2$ and $R_3$ are independently hydrogen or loweralkyl and $R_4$ and $R_5$ are independently halogen.

2. A compound of claim 1 wherein $R_1$ is hydrogen or lower alkyl, $R_2$ and $R_3$ are loweralkyl, and $R_4$ and $R_5$ are chlorine or fluorine.

3. A compound of claim 2 wherein $R_1$ is hydrogen, $R_2$ and $R_3$ are independently methyl or ethyl, $R_4$ is chlorine and $R_5$ is fluorine.

4. A compound of claim 3 which is 6-(N,N-dimethylaminomethylidineamino)-9-(2-chloro-6-fluorobenzyl)purine.

5. A method for the treatment of coccidiosis in poultry which comprises administering to poultry infected with coccidiosis an effective amount of a compound of claim 1.

6. A composition useful for the treatment of coccidiosis in poultry which comprises an effective amount of a compound of claim 1 and an inert carrier.

* * * * *